United States Patent
Andrady et al.

(10) Patent No.: US 12,257,329 B2
(45) Date of Patent: Mar. 25, 2025

(54) COMPOSITION FOR THE CONTROL OF ORAL MALODOR COMPOUNDS

(71) Applicant: Helix Science LLC, Apex, NC (US)

(72) Inventors: Anthony Andrady, Apex, NC (US); Milroy Codipilly, West End, NC (US)

(73) Assignee: Helix Science LLC, Apex, NC (US)

( * ) Notice: Subject to any disclaimer, the term of this patent is extended or adjusted under 35 U.S.C. 154(b) by 0 days.

(21) Appl. No.: 17/949,366

(22) Filed: Sep. 21, 2022

(65) Prior Publication Data

US 2023/0363989 A1    Nov. 16, 2023

Related U.S. Application Data

(60) Provisional application No. 63/341,149, filed on May 12, 2022.

(51) Int. Cl.
*A61K 8/27* (2006.01)
*A61K 8/60* (2006.01)
*A61K 8/73* (2006.01)
*A61Q 11/00* (2006.01)

(52) U.S. Cl.
CPC .................. *A61K 8/27* (2013.01); *A61K 8/60* (2013.01); *A61K 8/731* (2013.01); *A61Q 11/00* (2013.01)

(58) Field of Classification Search
CPC . A61K 8/735; A61K 8/60; A61K 8/19; A61K 8/0241; A61K 8/27; A61K 8/044; A61K 8/73; A61K 8/731; A61K 2800/413; A61Q 11/00
See application file for complete search history.

(56) References Cited

U.S. PATENT DOCUMENTS

2004/0091430 A1*  5/2004  Harwood .................. A61K 8/97
                                                          424/125
2014/0030314 A1*  1/2014  Larson .................. A61K 31/616
                                                          424/85.4

FOREIGN PATENT DOCUMENTS

| CN | 1377698 | * | 11/2002 |
| CN | 101176698 A | * | 5/2008 |
| JP | H10182390 | * | 7/1998 |
| MA | 29428 | * | 5/2008 |

* cited by examiner

*Primary Examiner* — Lezah Roberts
(74) *Attorney, Agent, or Firm* — Murthy Patent Law Inc.; Karthik Murthy

(57) ABSTRACT

An aqueous composition for removing oral malodor caused by volatile gaseous compounds present in the oral cavity is disclosed herein. The aqueous oral composition comprises one or more of metals selected from the group consisting of Silver, Gold, Zinc, Aluminum, Magnesium and Tin, wherein the metals are present as a stable aqueous nanoparticulate dispersion or a colloid, having an average metal particle size of 1-1000 nm. at a concentration between 1 to 100 ppm. The aqueous oral composition may also include metal particles that may be partially oxidized, by reaction with oxygen including that from air during manufacture or storage. The aqueous oral composition may also include a mucoadhesive polymer selected from a group of water-soluble polymers having an affinity to keratin. The aqueous oral composition may be a synergistic mixture of two or more metal nanoparticulate colloids.

17 Claims, 4 Drawing Sheets

Table 1: Reported ranking of 4 commercial mouthwashes and the test formulation disclosed herein by six subjects. (n=6)

| Mouthwash | 0 - No taste | 1- Mild taste | 2- moderate taste | 3- Strong taste | Description |
|---|---|---|---|---|---|
| Test Formulation | 6 | | | | No taste |
| Smart Mouth | | 6 | | | Astringent, chlorine |
| Close Up | | 6 | | | Menthol, cinnamon |
| Scope* | | | 5 | 1 | Phenolic |
| Listerine# | | | | 6 | Phenolic, thymol |

* contains 8% alcohol; # ~21.6% alcohol

FIG. 1

The particle size distribution of a colloidal suspension of zinc at a concentration of 36 ppm of the metal, determined using Nanoparticle Tracking Analysis.

The efficacy of colloidal zinc suspension in controlling hydrogen sulfide concentration in the oral cavity, as determined by Halimeter measurements before and after using the aqueous suspension as a rinse.

COMPOSITION FOR THE CONTROL OF ORAL MALODOR COMPOUNDS

FIELD OF INVENTION

Disclosed herein is a composition suitable for removing oral malodor caused by volatile gaseous compounds present in the oral cavity. The composition comprises of nanoscale particles of one or more metals that has an affinity to volatile gaseous compounds, especially sulfur compounds, with or without a mucoadhesive polymer, in an aqueous suspension.

BACKGROUND OF INVENTION

Halitosis, (bad breath or oral malodor) is a common problem that causes embarrassment and affect the quality of life of those with the condition and over 30% of the population are estimated to be affected by halitosis [Silva et al., 2018][1]. About 90% of halitosis originates in the oral cavity [Tangerman & Winkle, 2013][2] and is typically generated during sleep from bacterial activity encouraged by hyposalivation. Anaerobic bacterial species capable of metabolizing sulfur-containing amino acids such as cysteine or methionine that are generally present in mucosa, and concentrated on the lingual keratin biofilm, are responsible for the generation of oral malodor and in some instances gingivitis and periodontitis as well. An overgrowth of these microorganisms produce volatile sulfur compounds (VSCs) such as hydrogen sulphide and methanethiol the compounds in high concentrations and these are responsible for 90% of malodor related to halitosis [Tonzetich, 1977][3].

The Halimeter is a device manufactured by Interscan company in Simmy Valley, California, for measuring levels of volatile sulfur compounds (calibrated to $H_2S$) in oral cavity for detection of Halitosis. It has a measuring range of 0-1000 ppb of $H_2S$ at an accuracy of ±2% of the reading. A pump in the device pulls in a stream of air from the oral cavity and directs it over a chemical sensor element for the gas to estimate the $H_2S$ levels in the air stream. The model Halimeter BLU was used for this work as it is the most-used device for oral volatile sulfide measurements reported in the literature. Typically, the VSC levels in the oral cavity of a subject affected by Halitosis as measured by a Halimeter (http://halimeter.com/calibration-procedure) used according to manufacturers recommended methodology, is >110 ppb.

One approach employed in oral rinses used to mitigate the malodor is to use compounds to mask or cover up the odor using a compound that emits a stronger dominant but pleasant odor, as used in oral sprays or scented chewing gum products. A second approach is to use a chemical that reacts with the odor-causing chemical in the oral cavity to neutralize the malodor. The present invention falls into the latter category where a water-insoluble solid metal agent in suspension reacts with the odor-causing VSCs to neutralize the odor. Where a water-soluble chemical such as a metal salt is used for this purpose, it imparts a disagreeable taste to the oral rinse or other product and discourages its use. Dental dyschromia and taste alteration resulting from the water-soluble components present in conventional oral rinse preparations have been reported (Riapri et al., 2020).

Oral rinses intended to control malodor or halitosis are commercially available. Bacteriostatic or antibacterial species such as peroxides, oxidants, phenolics, iodine, methyl salicylate, menthol and soluble metal salts (e.g. stannous fluoride) dissolved in an alcohol solution can be used to address the problem in the long term [Linde, 2005][4]. For instance, oxidants such as peroxide or chlorites solutions might be used to create an oral environment where anaerobic bacteria do not thrive. Long-term use of these preparations may alter the oral microbial environment, with undesirable outcomes. For example, chlorhexidine, a synthetic biguanide cationic molecule, has a strong bactericidal and bacteriostatic action but its use results in dyschromia, taste alteration and plaque deposit (Jones, 2000[5]; Ripari et al., 2020[6].) Water soluble organic compounds that react with the VSCs in the oral cavity can also be used for the purpose.

Available oral rinses suffer from a common drawback in that they have astringent or bitter taste and sometimes an objectionable odor as well. Sweet and bitter perceptions are known to influence oral hygiene practices including the use of mouthwashes [Kaur et al., 2021][7]. These preparations also typically carry water-soluble chemicals that can be absorbed via the oral epithelium into the blood stream. They could be harmful if accidentally ingested (mouthwashes are not to be swallowed, but expectorated by the user). Some of the preparations may contain alcohol as a solvent that is also absorbed in the buccal cavity. Such sorption of chemicals from a routinely used preparation is undesirable as their long-term effects are not always known.

SUMMARY OF INVENTION

There is a need for an oral rinse or mouthwash that effectively controls malodor but with no disagreeable taste or smell associated with it. Ideally, the oral rinse should not be toxic by accidental ingestion and not include any alcohol or low any molecular-weight compounds absorbable via the oral mucosa. The present invention teaches an oral rinse based on colloidal metal, comprising especially of metal nanoparticles or colloids, in aqueous suspension as a tasteless, odorless, non-toxic and cost-effective, for controlling halitosis.

Disclosed herein is an aqueous oral composition that is capable of preventing or eliminating oral malador of humans caused by one or more physiological factors. The aqeuous oral composition disclosed herein comprises a metal particles selected from metals non-toxic to humans at the ppm level, that reacts at ambient temperature with volatile sulfur compounds responsible for oral malodor. The metals exist in a nanoparticulate form having a specific size of 1-2000 nm. The aqueous oral composition also comprises a mucoadhesive polymer that either binds or entangles the nanoparticles and place them in close proximity of the keratin layer in the oral cavity. In particular aspect of the aqueous oral composition, it comprises zinc metal in nanoparticle colloidal form and hyaluronic acid as the mucoadehesive polymer.

Colloidal metal particles have very high specific surface area consequent to their small particle sizes and provide a large area over which reaction with VSCs can occur. The reaction of the metal with VSC is therefore rapid enough to achieve neutralization in under 1 min., the typical time the rinse is in the oral cavity. Active sites on the metal surface bind one or more of the gaseous or volatile compounds responsible for malodor.

A single metal or a mix of several metals might be used to optimize the removal of specific VSCs in the oral cavity. For example, a colloid of zinc or of silver will act individually to mitigate the malodor but a mix of the two metal colloids in water, also shows the same or improved functionality. Primary mechanism of removal of the VSC is by chemical reaction although some surface adsorption of the gases may also contribute to the process. This refers to surface adsorption on the metal nanoparticles or colloidal metal particles. A composition of colloidal metal particles suspended in water, especially in the concentration range used in the disclosed invention, is completely tasteless and odorless. The concentration range of colloidal metal is 1 to 100 ppm. It does not have any astringent or bitter taste found in commercial formulations that discourage the consumers from using those regularly. However, where needed a fragrance or a flavor might be added to it for customer appeal.

Four commercial brands of mouthwashes sold in the USA were compared to a test formulation of zinc colloids in distilled water for their taste during use. Subjects who had not brushed their teeth nor consumed any food or drink including water, since waking up in the morning were used in this test. Each subject rinsed their mouth with ~3 mL of a mouthwash and rated its taste on a scale of 0 to 4, and also described the taste using a single word or phrase. The identity of the mouthwash was not available to the subjects. The results obtained shown in Table I of FIG. 1 show that the Test Formulation based on the patent has no taste while others have at least a mild taste.

More than one type of metal colloid can be used in oral rinse suspension in this invention. This has the advantage that certain metals may be particularly effective in removing specific gases and/or odorous compounds in the VSC. In one embodiment of this invention more than one type of metal colloid is used in the same suspension in water; for instance a mixture of silver and zinc colloids might be used. This composition removes at least one odorous sulfur compound from the oral malodor compounds among the VSCs.

One objective of this invention is to ensure that the oral rinse provides a longer-term control of malodor. Oral rinses including metal particle suspensions remove VSCs that are present in the oral cavity at the time of use. The residual active compounds in the oral rinse may be inadequate to provide continuing malodor removal to counter subsequent slow production of VSCs produced by oral flora over time. It is the biofilm of anaerobic bacteria residing on lingual surface on the keratin layer that is mostly responsible for the generation of VSCs. One object of the present invention is to includes a water soluble polymer that readily associates with the keratin surface. Metal colloid particles physically entrained in this polymer will be carried to and deposited on the keratin layer on the tongue without being readily rinsed out, providing continuing VSC control as well as bacteriostatic action. Bacteriostatic action against malodor forming as well as other undesirable bacterial species in the oral cavity can help counter hailtosis.

A muco-adhesive or keratinophilic polymer that also has a few acid functionalities such as hylauronic acid is the preferred polymer as the carboxylic acid groups on the polymer have an affinity to the positively charged nanoparticle surface. Consequent electrostatic interaction further enhances the entrainment of the metal colloid by the polymer and facilitate its deposition on keratin surfaces. Polymers are odorless and tasteless; the molecular size of polymers is too large to contribute either to the smell or taste of the formulation.

All functional components of the disclosed oral rinse are non-toxic and are used in food products or as healthcare supplements at or lower than the concentrations used here. Any accidental ingestion of these compounds will therefore not present any health problem to the user. None of these compounds can be absorbed into the blood stream via the oral mucosa because of their molecular particle size. None of the constituents are known to have any adverse effect on the oral mucosal or other tissue at the concentrations used.

While an oral rinse is the primary application disclosed here another objective of the invention is to use the same technology in other person-care and oral products. The base composition can be used in dentifrices, chewing gum, dental floss, mouth freshener sheets and oral spray formulations intended to control halitosis related malodor.

The foregoing and other features and advantages will become further apparent from the following detailed description of the preferred embodiments read in conjunction with the drawings.

BRIEF DESCRIPTION OF FIGURES

FIG. 1: Table 1 shows the reported ranking of 4 commercial mouthwashes and the test formulation disclosed herein by six subjects.

DETAILED DESCRIPTION THE INVENTION

Figure 2:
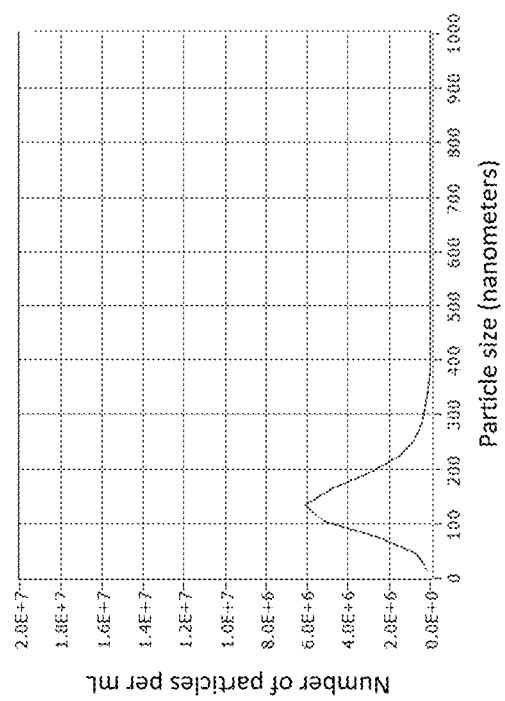
FIG. 2: The particle size distribution of a colloidal suspension of zinc at a concentration of 36 ppm of the metal, determined using Nanoparticle Tracking Analysis.

The stable metal colloids referred to in this invention are collections of polydisperse nanoscale particles mostly below the size of 1000 nm in diameter, ideally below 500 nm in diameter. Colloidal suspensions are polydiverse in size when manufactured. In the present invention the average particle size is polydiverse. The lower the average diameter of a particle, the higher the surface area per unit mass of the metal particles. A higher surface area is desirable as the reaction of metal with hydrogen sulfide [$H_2S$] gas or another volatile gas is an exclusively surface reaction. Metal colloids in aqueous suspension can be generally synthesized by three chemical methods; chemical reduction of metal salt precursors, electrochemical synthesis, and controlled decomposition of organometallic compounds. Metal colloids produced by any of these techniques may be used in this invention. The entire surface of a nanoparticle is available as an area of active sites for reaction with VSCs, especially hydrogen sulfide [$H_2S$] gas. Once a site has reacted with a VSC molecule it is inactive and cannot react with a second molecule. The particles therefore have a finite capacity to bind the VSC molecules. Colloidal particles have very high surface area; the specific surface area of a 1000 nm spherical particle~2 sq. m./g while that of a 100 nm~30 sq. m./g. These high values for surface area ensure rapid reaction with VSC that is critical for a mouthwash that is left in the oral cavity for only about 60 sec.

Metal particles that are larger than colloidal (e.g. metal dust <5000) can also be used in place of the disclosed invention, however, as the particle size increases the time needed to remove the VSCs or the rinse time will increase. Also, the rinse may have to be agitated before use to overcome sedimentation. Alternatively, the density of the additives might be dissolved in the water to increase the density of solution to allow better suspension of the metal particles.

Examples of metal colloids that can be used in this invention include, without limitation, copper, silver, gold, iron, zinc, aluminum, magnesium, tin and manganese. The reduction potential of the metal gives some indication of its reactivity and can be used to assess their usefulness to remove hydrogen sulfide. Ranking some of the metals according to their reduction potential: Gold (1.69 V) and Silver (0.80 V) are both likely to be less reactive than zinc (−0.76 V). Iron (−0.44 V), though less reactive relative to zinc, can still be good candidate for the purpose of this invention.

Common metals such as silver, zinc, tin, copper and iron as well as their oxides are well known to react with hydrogen sulfide and volatile organic sulfides under a variety of conditions. For instance, the tarnishing of silver in air at ambient temperature is attributed to slow reaction with trace $H_2S$ in air. The advantage of using the colloidal form of metal is fast reaction with sulfides including VSCs at ambient temperature. Rapid reaction is important as the oral rinse is typically in the mouth for only about a minute. Several non-toxic metals known to react rapidly with the gas including Zinc and Silver, are available as relatively low-cost colloid. Commercial stabilized colloids of these are available at concentrations of ~36 ppm in distilled water. These are the preferred metal colloids used in this invention.

Depending on their shelf life, slow oxidation of these metal particles in aqueous suspension may occur especially where the suspensions do not have any anti-oxidant additives designed to minimize oxidation. The partial surface oxidation of the metal nanoparticle does not impact the main functionality of their reaction with VSC molecules, as both the metal nanoparticles and their oxides are highly reactive with VSCs, especially $H_2S$. Metal colloids or nanoparticles referred to herein refer to either the metal nanoparticles or oxidized nanoparticles will all or some of their surface metal atoms converted to their oxides.

In another embodiment of the invention, an aqueous suspension of a single metal colloid, such as a zinc colloid, with an average particle size between 10 and 1000 nm, at a concentration of 1-500 ppm is used as the malodor removing mouthwash. The composition is prepared by diluting a commercially-available or custom-manufactured zinc colloid concentrate with distilled water, with stirring.

The Zeta View is a nanoparticle tracking analysis (NTA) instrument for measuring hydrodynamic particle size and the zeta potential nanoscale particles in suspension. NTA works by tracking particle motion via laser light scattering to assess the mean displacement of particles under Brownian motion. This allows the instrument to calculate the number of particles within the cell volume for particles in the size range of 30-600 nm at an accuracy of ±5%. NTA technique is used to determine nanoparticle concentrations in suspension.

FIG. 2 is a particle size distribution curve obtained using Nanoparticle Tracking Analysis, measured with a Zetaview instrument (Analytic, Cambridge, UK) of zinc nanoparticles and possibly their aggregates, at 5.0 E08 particles/mL of suspension with a mean particle diameter was 144.9 (std. deviation 39). The metal colloids generally carry a surface positive charge wherein the zeta potential of the colloid was +1 to +50 mV indicating the particles carry a positive surface charge at the test pH of 7.0. The surface charge is an important attribute of the metal particles as positively charged particles adhere better to the oral mucosa that carries a negative surface charge.

Figure 3:
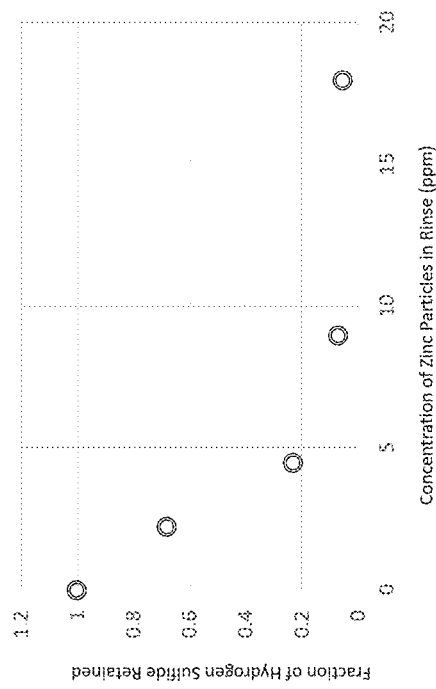
FIG. 3: The efficacy of colloidal zinc suspension in controlling hydrogen sulfide concentration in the oral cavity, as determined by Halimeter measurements before and after using the aqueous suspension as a rinse.

Another embodiment of the invention uses a suspension of zinc colloidal particles of a median size of 145 nm in distilled water as the basic composition of the oral rinse. Efficacy of this composition was compared to that at a range of concentrations using healthy subjects. None of the subjects had brushed their teeth nor consumed any food or drink including water, since waking up in the morning. The concentrations of $H_2S$ gas in the oral cavity of the subjects was measured with a commercial Halimeter BLU (Interscan corporation, Simmy Valley, CA) following the operational procedure suggested by the manufacturer. The subject first rinsed the mouth for 60 sec. with an aqueous solution of 0.05 weight % L-Cisteine that stimulated the mucosal bacterial flora to produce copious amounts of VSCs, increasing the measured background level of the gas in the oral cavity from <100 ppb to over 1000 ppb. This initial value of hydrogen sulfide, $C_1$, was measured using the Halimeter as the mean of 3 consecutive readings taken 30 sec. apart. Typically ~700-900 ppb of sulfide was detected in the oral cavity using the instrument, after the subject had rinsed with cysteine solution for one minute. Subjects reported a sulfurous taste in their mouth after the rinse. The subjects then rinsed their mouth again with either a control solution of distilled water or with a test composition of nano-zinc particles in distilled water (at concentrations in the range of 0-18 ppm) for a one-minute period and repeated the measurement of $H_2S$ gas. The value of concentration $C_2$, the mean of 3 consecutive readings, taken 30 sec. apart was also recorded. The efficacy of the oral composition is expressed as the percent reduction in volatile sulfides, $\{(C_1-C_2)/C_1\}\times 100$. The data from a typical experiment is shown in FIG. 3. Using the oral composition with a concentration > of zinc as a 60-second rinse, reduced the volatile sulfides in the oral cavity by >90% as seen from FIG. 3 while the control solution of distilled water resulted in no such decrease.

In one embodiment of this invention a 9 ppm suspension of colloidal elemental silver (Ag) in distilled water was used as the oral rinse. The same subjects as in were used on different days for this assessment. The cisteine-stimulated oral VSCs in breath was measured using the Halimeter as $C_1$ and the value after subsequent rinsing with the silver-colloid oral rinse for one minute was recorded as $C_2$. Comparing the 2 values a 95% reduction in VSCs was obtained.

In one embodiment of the invention a water-soluble a keratinophilic polymer is added to the oral rinse composition. The linear chains of the polymer tend to entrain the nanoparticles and any carboxylic acid groups present on the polymer chain. The linear chains of the polymer are attracted to the positively charged nanoparticle surface. The polymer-nanoparticle electrostatic network that results from the interaction tends to adhere to the keratin layer where the malodor producing bacterial flora reside. The location of the nanoparticle-polymer network in close proximity to the keratin layer provides a more effective and longer period of malodor prevention. The action of bacteriostaic or bacteriocidal compounds depend on their concentration. The odor-causing bacteria are located in the keratin layer in the oral cavity. The closer the bacteriostatic compound to the bacteria, the greater its effectiveness. Instead of being washed off by saliva, the nanoparticle-polymer network is held close to the keratin layer, and therefore can provide action (malodor prevention) for a longer period of time.

Only the zinc nanoparticles provide bacteriostatic action. The polymer molecules, being attracted to keratin layer, hold the zinc nanoparticles. Water-soluble polymers, or their oligomers, including but not limited to carboxymethyl cellulose, methyl cellulose, hydroxypropyl cellulose, hyaluronic acid, hydroxy propyl methyl cellulose, soluble starches, chitosan, xanthan gum, glen gum, guar gum or carrageenan, can be used in the formulation.

Figure 4:
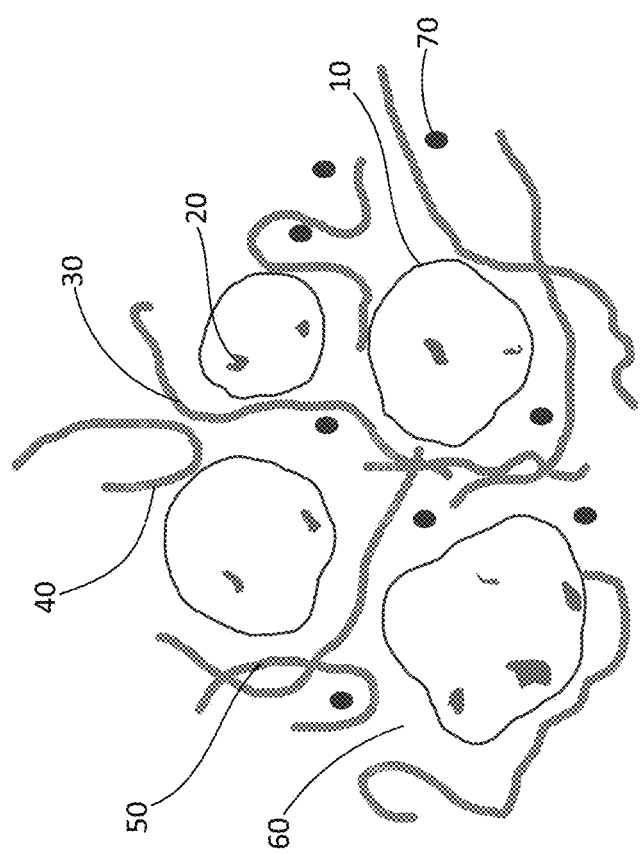
FIG. 4: Drawing of an ensemble of metal nanoparticles and keratinophilic polymer that can also interact with the nanoparticle, used in one embodiment of this invention.

FIG. 4 is a diagram (not to scale) representing an ensemble of metal nanoparticles and the keratinophilic polymer molecules in aqeuous suspension. The metal nanoparticle 10 is typically in the average size of <1000 nm and is dispersed in aqeuous medium 60 where it can move around by Brownian motion. The elemental metal surface of the nanoparticle may be partially oxidized due to exposure to atmospheric oxygen trapped in the headspace of the container, giving rise to surface regions 20 of the metal oxide. This assumes the composition has no antioxidant to control oxidation. The keratinophilic molecule 30, as in the case of hylauronic acid, may carry some negatively charged groups allowing it to electrostatically bind to nanoparticle surface at some points 40, or can be free in suspension 50. Depending on its concentration, the polymer and nanoparticle may form partial aggregates with an affinity towards oral keratin layer where the malodor forming bacteria reside. Low molecular weight additives such as antioxidants, colorants or flavor agents 70 if present will remain in solution.

In one embodiment of the invention, up to 1 wt % of carbon in the form of carbon powder, activated charcoal, carbon microfiber or engineered carbons such as carbon nanotubes might be incorporated into the composition as a supporting functional material. Carbons adsorb volatile sulfides without any reaction and therefore help control oral malodor quickly. Its presence in the oral rinse accelerates the removal of volatile sulfides.

In one embodiment of the invention a 0.02 wt. % of a water-soluble keratinophilic polymer, hyaluronic acid, was dissolved in the test composition of zinc colloidal suspension. This additive is expected to facilitate higher retention of the residual active zinc in the oral cavity, after rinsing, as a concentration of 9 ppm zinc nanoparticle suspension will use only a small fraction of the metal to neutralize the less than 1 ppm of sulfide in the oral cavity. The amount of elemental zinc present in the starting composition and that after being swished around in the mouth for 1 min. was measured using the inductively coupled plasma-mass spectrometry (ICP-MS) technique.

The recovery of zinc in post-rinse solution decreased from about 10% for no additive and 5-8% with the hyaluronic acid. By using the keratinophilic polymer in the formulation, more of the zinc nanoparticles were retained in the oral cavity after the rinse, providing continued malodor suppression, and bacteriostatic control against malodor forming as well as other undesirable bacterial species in the oral cavity.

The metal colloids {as well as the metal nanoparticle keratinophilic polymer networks} described herein can be used in other oral care products to control oral malodor. In another embodiment of the invention the metal colloids is compounded into tooth paste formulations. As the formulation is water based it can be readily incorporated into dentifrice and does not interfere with the action or the bioavailability of the fluoride used in those products. In another embodiment of the metal colloid suspension may be used in denture adhesive pastes, powders or gels to impart malodor control properties to those products. In yet another embodiment of the invention toothbrush bristles, floss materials and flossing brush devices might include the colloidal metal formulation into the plastic materials. In this last application only the surface-particles will provide malodor control.

In another embodiment of the invention, the metal colloids as well as the metal colloid-keratinophilic polymer networks described herein, can be incorporated into products used for temporary relief of malodor including malodor-controlling chewing gum, oral sprays, edible plastic films and mucoadhesive saliva-soluble films that can be placed in the oral cavity as needed. In another embodiment of the invention the metal colloid can be aerosolized by packaging it with a suitable propellant in a spray device. The malodor-controlling spray can be used for fast control of oral malodor. The metals used, especially at the concentrations needed for effective functionality, are non-toxic, allowing this mode of use.

In another embodiment of the invention the colloidal metal system might be used in a test strip to detect halitosis in preventative dentistry. The metal colloid selected in this case forms a colored product on reacting with $H_2S$ gas that is the primary component of VSCs. For instance lead or copper colloids yield a black coloration, while antimony yields a bright orange coloration, even at low levels of the gas. A transparent plastic or glass tube that the subject blows into, carries the colloidal composition on porous paper or cotton wool substrate. Porous paper or cotton wool substrate can be used as a convenient design of such a device.

Example 1

A 9 ppm solution of zinc colloid is prepared in distilled water by diluting a stock solution of 250 ppm of the colloid obtained commercially (from Silver Mountain Minerals, Hurricane, Utah) at ambient temperature. This odorless tasteless suspension was tested as a mouth rinse by swirling 3 mL of the liquid in the oral cavity for a period of one minute. This is the formulation one referred to in FIG. 3.

Example 2

A 9 ppm solution of zinc colloid is prepared in distilled water by diluting a stock solution of 250 ppm of the colloid obtained commercially (from Silver Mountain Minerals, Hurricane, Utah) at ambient temperature. A quantity of food-grade hyaluronic acid (HA) (from Quality Products Direct, American Forks, Utah) was dissolved in the colloid suspension to obtain a concentration of 0.01 w/v percent of HA in the mouth rinse. The rinse when used as in example 1 is effective in controlling oral malodor.

While the embodiments of this invention described are presently preferred, various modifications and improvements can be made to the oral rinse or other formulations without departing from the spirit and scope of the invention. The scope of the invention is indicated by the appended claims and all changes that fall within the meaning and range of equivalents are intended to be embraced therein.

CITATIONS

[1] Silva M F, Leite F R M, Ferreira L B, Pola N M, Scannapieco F A, Demarco F F, Nascimento G G. Estimated prevalence of halitosis: a systematic review and meta-regression analysis. Clin Oral Investig. 2018, 22 (1): 47-55

[2] Albert Tangerman & Edwin G. Winkel (2013) Volatile Sulfur Compounds as The Cause of Bad Breath: A Review, Phosphorus, Sulfur, and Silicon and the Related Elements, 188:4, 396-402, DOI

[3] Tonzetich J 1977 Production and origin of oral malodor: a review of mechanisms and methods of analysis J. Periodontol. 48 13-20

[4] Nancy Linde, in Encyclopedia of Toxicology (Second Edition), 2005

[5] Jones C G. Chlorhexidine: is it still the gold standard?. Periodontol 2000 1997; 15:55-62

[6] Francesca Ripari, Alessia Cera, Monica Freda, Giulia Zumbo, Francesca Zara, Iole Vozza (2020) Tea Tree Oil versus Chlorhexidine Mouthwash in Treatment of Gingivitis: A Pilot Randomized, Double Blinded Clinical Trial. Eur J Dent 2020; 14 (01): 055-062

[7]Kaur, K., Sculley, D., Veysey, M. et al. Bitter and sweet taste perception: relationships to self-reported oral hygiene habits and oral health status in a survey of Australian adults. *BMC Oral Health* 21, 553 (2021).

What is claimed is:

1. An aqueous composition for controlling halitosis comprising one or more elemental metals comprising zinc, wherein the one or more elemental metals does not include oxides of the one or more elemental metals; wherein the one or more elemental metals is present as a stable aqueous nanoparticulate suspension or a colloid, having an average metal particle size of 1-1000 nm at a concentration between 1 to 100 ppm, and a mucoadhesive polymer comprising hyaluronic acid, wherein the mucoadhesive polymer is water soluble polymer having an affinity to keratin.

2. An aqueous composition for controlling halitosis comprising: one or more elemental metals comprising zinc, wherein the one or more elemental metals does not include oxides of the one or more elemental metals; wherein the one or more elemental metals is present as a stable aqueous nanoparticulate suspension or a colloid, having an average metal particle size of 1-1000 nm at a concentration between 1 to 100 ppm, and a mucoadhesive polymer selected from a group of water-soluble polymers having an affinity to keratin; wherein the zinc is present as a nanoparticulate colloid having a particle size of 1-500 nm; and wherein the mucoadhesive polymer comprises hyaluronic acid present at a concentration of 0.001 to 0.02 weight percent.

3. An aqueous composition for controlling halitosis comprising a metal, wherein the metal is not an oxide, and wherein the metal is present as a stable aqueous nanoparticulate colloid having an average metal particle size of 1-1000 nm at a concentration between 1 to 100 ppm; and a mucoadhesive polymer comprising water-soluble polymers having an affinity to keratin, at a concentration of 0.001 to 0.05 weight percent; wherein the mucoadhesive polymer comprises hyaluronic acid present in an amount of 0.02% weight percent; wherein the metal comprises zinc, wherein the metal is zinc having an average particle size of 1-500 nm and in an amount of 20-30 ppm and a functional agent in the form of adsorbent material for organic compounds; wherein the functional agent is multi-walled carbon nanotubes and is included in the formulation in an amount of 0 to 0.5 wt. percent.

4. An oral rinse for controlling halitosis comprising zinc; wherein the zinc is not an oxide; wherein zinc is present as a stable aqueous suspension of nanoparticles or a colloid having an average metal particle size of 1-1000 nm at a concentration between 1 to 100 ppm, one or more mucoadhesive polymers selected from a group consisting of water-soluble polymers having an affinity to keratin; wherein the one or more mucoadhesive polymers binds or entangles the nanoparticles or the colloid and places them in close proximity to a keratin layer in the oral cavity, and formulating agents comprising cosmetically-acceptable adjuvants, auxiliaries, anti-oxidants, colorants, fragrances, additives and fluorides that contribute to oral health.

5. The aqueous oral composition of claim 3, wherein the metal further comprises:
Gold.

6. The aqueous oral composition of claim 3, wherein the metal further comprises:
Aluminum.

7. The aqueous oral composition of claim 3, wherein the metal further comprises:
Magnesium.

8. The aqueous oral composition of claim 3, wherein the metal further comprises:
Tin.

9. The aqueous oral composition of claim 3, wherein the mucoadhesive polymer further comprises
carboxymethyl cellulose.

10. The aqueous oral composition of claim 3, wherein the mucoadhesive polymer further comprises
methyl cellulose.

11. The aqueous oral composition of claim 3, wherein the mucoadhesive polymer further comprises further comprising:
hydroxy propyl methyl cellulose.

12. The aqueous oral composition of claim 3, wherein the mucoadhesive polymer further comprises
soluble starches.

13. The aqueous oral composition of claim 3, wherein the mucoadhesive polymer further comprises
chitosan.

14. The aqueous oral composition of claim 3, wherein the mucoadhesive polymer further comprises
xanthan gum.

15. The aqueous oral composition of claim 3, wherein the mucoadhesive polymer further comprises
guar gum.

16. The aqueous oral composition of claim 3, wherein the mucoadhesive polymer further comprises
carrageenan.

17. The aqueous oral composition of claim 3, wherein the mucoadhesive polymer further comprises carboxymethyl cellulose, methylcellulose, hydroxypropyl cellulose, hydroxy propyl methyl cellulose, soluble starches, chitosan, xanthan gum, guar gum or carrageenan, or a mixture thereof, and wherein the mucoadhesive polymer is present at a concentration of 0.001 to 0.05 weight percentage.

\* \* \* \* \*